United States Patent [19]

Lucas et al.

[11] 4,392,848
[45] Jul. 12, 1983

[54] CATHETERIZATION

[75] Inventors: Donald S. Lucas; Roger L. Stone, both of Fairfield; Eugene R. Cooper, Cincinnati, all of Ohio

[73] Assignee: The Procter & Gamble Company, Cincinnati, Ohio

[21] Appl. No.: 51,477

[22] Filed: Jun. 25, 1979

[51] Int. Cl.$^3$ .............................................. A61M 5/00
[52] U.S. Cl. .................................... 604/53; 604/257; 604/265
[58] Field of Search ........... 128/213 A, 213 R, 214 R, 128/214.2, 214.4, 221, 348, 349, 260, 1 R, 130; 424/317, 177

[56] References Cited

U.S. PATENT DOCUMENTS

| | | | |
|---|---|---|---|
| 1,772,975 | 8/1930 | Wieland . | |
| 2,154,499 | 4/1939 | Hoffmann et al. | 99/90 |
| 2,190,714 | 2/1940 | Hoffmann et al. | 99/224 |
| 2,466,663 | 4/1949 | Russ et al. | 167/58 |
| 2,729,586 | 3/1956 | Peck | 424/177 |
| 3,279,996 | 10/1966 | Long et al. | 167/82 |
| 3,404,987 | 10/1968 | Kooistra et al. | 99/150 |
| 3,434,869 | 3/1969 | Davidson | 117/94 |
| 3,524,447 | 8/1970 | Evans et al. | 128/348 |
| 3,566,874 | 3/1971 | Shepherd et al. | 128/349 |
| 3,598,126 | 8/1971 | Wepsic | 128/348 |
| 3,598,127 | 8/1971 | Wepsic | 128/349 |
| 3,663,965 | 5/1972 | Lee et al. | 3/1 |
| 3,695,921 | 10/1972 | Shepherd et al. | 117/72 |
| 3,699,956 | 10/1972 | Kitrilakis et al. | 128/348 |
| 3,708,324 | 1/1973 | Stebleton | 117/47 R |
| 3,767,803 | 10/1973 | Nürnberg | 424/317 |
| 3,854,480 | 12/1974 | Zaffaroni . | |
| 3,886,947 | 6/1975 | Sawyer | 128/348 |
| 3,926,705 | 12/1975 | Todd | 156/155 |
| 4,002,775 | 1/1977 | Kabara . | |
| 4,159,720 | 7/1979 | Burton | 128/213 R |
| 4,186,745 | 2/1980 | Lewis et al. | 128/260 |
| 4,280,500 | 7/1981 | Ono | 128/348 |

FOREIGN PATENT DOCUMENTS

| | | | |
|---|---|---|---|
| 2720776 | 11/1978 | Fed. Rep. of Germany . | |
| 2813750 | 4/1979 | Fed. Rep. of Germany | 128/348 |
| 731097 | 6/1955 | United Kingdom . | |
| 1063870 | 3/1967 | United Kingdom . | |
| 1348340 | 3/1974 | United Kingdom . | |

OTHER PUBLICATIONS

Kabara, J. J., "Lipids as Safe and Effective Antimicrobial Agents for Cosmetics and Pharmaceuticals"; Cosmetics and Perfumery, vol. 9, May 1975, pp. 21–25.
The Merck Index, 7th Ed., p. 1117, "Zinc Propionate".

Primary Examiner—Richard J. Apley
Assistant Examiner—T. J. Wallen
Attorney, Agent, or Firm—Michael J. Roth; Michael P. Brennan; Steven J. Goldstein

[57] ABSTRACT

At least part of an antimicrobial catheter for use in humans and lower animals comprises a permeable polymer. The polymer must be in contact with both the environment external to the catheter and with a liquid reservoir of antimicrobial agent flowing through the lumen of the catheter, said liquid reservoir comprising an aqueous solution containing at least a minimum lethal concentration of a straight-chain carboxylic acid or carboxylic acid salt having from 4 to 9 carbon atoms. In use, the antimicrobial agent diffuses from the liquid reservoir through the polymer and provides a zone of microbial inhibition around the external surface of the catheter. The invention thus prevents nosocomial infections resulting from the use of catheters by inhibiting microorganisms at and around the placement site of the catheter when the catheter is inserted into the body of a human or lower animal.

20 Claims, No Drawings

CATHETERIZATION

TECHNICAL FIELD

The administration of intravenous (I.V.) solutions of various types to humans and lower animals is required in the treatment of a variety of disease states. Yet, because the intravenous catheter provides a direct path from the environment to the patient's bloodstream, the risk of bacterial or mycotic contamination and sepsis is especially acute during I.V. therapy. It has long been recognized that administration of intravenous solutions, which involves repeated changes of exhausted solution containers, removal and reinsertion of catheters, and other physical manipulations and adjustments of the intravenous apparatus which provide opportunities for contamination, can lead to full body mycotic and/or bacterial infection if sterile conditions are not rigorously maintained.

Similarly, decisions regarding catheterization of the urinary bladder and prolonged endotracheal intubation (for respiratory support) are always influenced by considerations of the high risk of infection occasioned by prolonged contact of foreign objects (the catheter) with mucosal surfaces where pathogenic bacteria and fungi are normally present.

Finally, a wide variety of surgical conditions require the insertion of drains or catheters into normally inaccessible parts of the body through artificial, surgically-created passages. Examples include pneumothorax, hydrocephalus, and biliary tract surgery. In these cases, although an infection is less likely, it is usually a serious complication when it occurs so that patients with these problems are frequently treated with prophylatic courses of antibiotics, with all the attendant risks of allergy, toxicity, superinfection and development of resistant strains of bacteria.

Physicians have long decried the fact that progress in developing treatment regimens for burn victims, comatose patients, patients who have undergone gastrointestinal surgery, cancer victims, and other patients whose natural barriers to infection have been compromised is being hindered by the problem of sepsis. The following references illustrate the current state of the medical art in this area.

"Infection is a significant hazard, and disseminated fungal infections has been a particularly frequent and dread complication of total parenteral nutrition." Goldmann and Maki, "Infection Control and Parenteral Nutrition", *Journal of American Medical Association*, 223, 12 (1973), pages 1360-64.

"Disseminated candidiasis is an increasingly common cause of morbidity and death, especially in hospital patients..." Letter to the Editor, *The Lancet*, Nov. 13, 1976, page 1084.

At least 10 million hospital patients receive I.V. therapy yearly. Septicemia rates as high as 8% are seen in some hospitals. Maki, "Preventing Infection In Intravenous Therapy", *Hospital Practice*, April, 1976, pages 95-104.

"On the clinical front the approach to infection with yeasts is far less purposeful; and this is well illustrated by candida, which is evidently an increasingly common cause of morbidity and death, especially in hospital patients." "Troublesome Candida", *The Lancet*, July 26, 1975, page 167.

Quie, "Fungal Septicemia in Patients Receiving Parenteral Hyperalimentation", *New England Journal of Medicine*, 285, 22 (1971), pages 1221-25.

"... [H]alf of all nosocomial infections were related to devices used to treat patients. The same intravenous lines that deliver drugs or nutrients to the bloodstream are also conduits for bacteria ... " Dr. Dennis Maki, *The New York Times*, June 5, 1978.

Physicians are apparently meeting this problem by curtailing or even discontinuing the portion of their therapeutic regimen which involves interruption of the body's antimicrobial barriers by foreign objects such as I.V. catheters, urinary catheters, and the like. Even when such devices are employed, as they frequently are, the attendant high risk of infection is always a consideration which enters physicians' evaluation of the risk/benefit ratio of the chosen course of therapy.

Another approach has been the widespread adoption of more stringent sterility and "good housekeeping" standards for hospitals. Unfortunately, fungi and bacteria remain ubiquitous in the hospital environment. Fortunately, even most pathogenic bacteria and fungi are harmless to humans and lower animals, unless the body's natural barriers to infection break down. This can occur by a break in skin integrity as in a surgical incision or the insertion of an intravenous catheter, or by the interference of a foreign body with the group of normal flora which inhabit the mucous membranes and other epithelialized areas of the body as in the case of urinary catheters. Current hypotheses hold that infectious microorganisms migrate from the point of entry into the body inward along catheters, drains, and the like, until they reach the bloodstream or other tissues which provide a fertile medium for growth. But regardless of the route, once infectious microorganisms are internalized, massive infestation throughout the body can result.

Bacterial sepsis can generally be treated successfully with antibiotics, but a complete treatment regimen can be expensive and time consuming. In addition, antibiotic therapy is often complicated by superinfections and, increasingly, the appearance of antibiotic-resistant pathogenic strains. Mycotic infections (fungi, molds, yeasts), typically occasioned by extremely high fevers, are unusually refractory to commonly employed antibiotics and as a result are often fatal.

In light of the foregoing, it is clear that when a break in the body's natural barriers to infection is necessary, prevention of infection is always preferable to treatment.

From the foregoing it can also be seen that an ideal method of preventing the infections associated with the use of catheters and similar medical devices is to establish an antimicrobial barrier on and around such devices, so that bacteria are unable to migrate along them and into the body.

The present invention provides a method of preventing nosocomial infections resulting from the use of catheters by achieving microbial inhibition at and around the catheter placement site.

The present invention also provides an article of manufacture especially adapted for use in catheterization of humans or lower animals, comprising, for example, a catheter of carboxylic acid-permeable polymer, in contact with both the environment external to the catheter and with a liquid reservoir of antimicrobial agent flowing through the lumen of the catheter, wherein the reservoir of antimicrobial agent comprises an aqueous solution containing at least a minimum lethal concentration of a straight chain carboxylic acid or acid salt having from 4 to 9 carbon atoms.

BACKGROUND ART

The use of antimicrobials to inhibit the growth of bacteria, fungi and molds in food compositions for oral ingestion is well known. For example, sodium propionate is routinely added to commercial bread to inhibit mold. In spite of the body of literature on this general topic, workers in the medical/veterinary sciences do not appear to have appreciated the special benefits which are afforded when carboxylate antimicrobials are used in the manner of the present invention. In particular, the use of carboxylate antimicrobials with articles of the present type which are designed to allow diffusion of the antimicrobial agent through the walls of the article to provide a zone of microbial inhibition in the tissue surrounding the article has not been suggested heretofore. This is indeed surprising, in light of the pressing need to avoid microbial contamination and possible sepsis in patients undergoing treatment regimens where there is any likelihood of direct communication between the external environment and normally protected tissues and body cavities.

This oversight on the part of the medical community may have occurred because medical science is only now coming to grips with the problem of massive sepsis due to newer medical techniques such as total parenteral nutrition. Equally likely is that the carboxylates have been passed over as ineffective antimicrobials in light of the confused state of recent literature.

The doctoral dissertation of Roger L. Stone, entitled "The Requirements for Metabolizable Energy and Nitrogen for Maintenance in Parenterally Fed Sheep", The Ohio State University, published August, 1975, page 37, discloses the use of propionic acid in intravenous solutions. These solutions were administered via a silicone rubber catheter, but no mention is made of any antimicrobial effect of the acid-plus-catheter combination.

U.S. Pat. No. 2,729,586, issued Jan. 3, 1956 to S. M. Peck, describes therapeutic compositions comprising water-soluble chlorophyll and at least one salt of a $C_3$–$C_{11}$ monocarboxylic acid.

U.S. Pat. No. 4,002,775, issued Jan. 11, 1977, to J. J. Kabara, describes fatty acids and derivatives as antimicrobial agents. According to the Kabara patent, neither caproic (hexanoic) nor caprylic (octanoic) acid are inhibitory to any of the microorganisms under the test conditions. Yet, properly used in the manner disclosed herein, these two carboxylate materials have now been found to be particularly potent, yet safe and highly preferred, antimicrobial agents which are capable of diffusion through silicone polymers and other elastomers to provide a zone of microbial inhibition around catheters, and the like.

U.S. Pat. No. 2,154,449, Hoffman, et al., 1939, describes the use of aliphatic carboxylic acids ($C_3$–$C_{12}$) or their salts as mold inhibitors in foods. The patent teaches the use of these acids to protect materials susceptible to mold, including tobacco, paper, leather, textiles, etc.

U.S. Pat. No. 2,190,714, to Hoffman, et al., 1940, claims a method of inhibiting mold growth in food products other than margarine and sour dough bread by adding a $C_3$–$C_{12}$ carboxylic acid thereto.

U.S. Pat. No. 3,404,987, to Kooistra and Troller, 1968, discloses and claims an antimicrobial composition containing 110 parts by weight of an edible mineral salt (iron, manganese, zinc, tin, or silver) and 1–150 parts by weight of an edible acid preservative substance, specifically including propionic acid. The metal salts are taught to impart enhanced and sustained antimicrobial/antifungal activity to the acid preservative substance.

U.S. Pat. No. 1,772,975, Wieland, 1930, teaches the use of solutions of lactic acid, acetic acid, or homologues thereof, as antiseptics at properly adjusted pH's.

U.S. Pat. No. 2,466,663, Russ, et al., 1949, describes the use of caprylic (octanoic) acid to combat mycotic infections or growths. This acid may be used topically as a liquid, ointment or butter for the treatment of surface infectants. It is also taught to be useful for combatting internal infections by injecting intravenously.

The Merck Index, 7th Ed., page 1117, teaches that zinc propionate is used as a fungicide on adhesive tape to reduce plaster irritation caused by molds, fungi and bacterial action.

German Pat. No. 2,720,776, issued Nov. 23, 1978 to Akiyama, describes a urinary catheter for long-term use which is made of an elastomer or polymer and which gives off bactericidal metal ions.

U.S. Pat. No. 3,434,869, issued Mar. 25, 1969 to J. B. Davidson, describes a urinary catheter of organic rubber with a surface coating of elastomeric silicone containing a silica filler.

U.S. Pat. No. 3,598,127, issued Aug. 10, 1971 to J. G. Wepsic, describes a catheter having an inner tube of non-permeable rubber formed with V-shaped grooves extending along its length on the outside, carrying antibacterial agents permeable through polysiloxane rubber that surrounds the V-shaped grooves. The antibacterials mentioned in this patent include neomycin, bacitracin, sulfa, mandelamine, zephiran, hexachlorophene, and furadantoin.

Numerous patents cover catheters and similar articles of various designs and materials. Examples include the following.

U.S. Pat. No. 3,699,956, to S. Kitrilakis, et al., Oct. 24, 1972, discloses a percutaneous lead device including an element for preventing bacterial infection caused by implanting the lead through the skin.

U.S. Pat. No. 3,695,921, issued Oct. 3, 1972, to T. H. Shepherd, et al., describes a catheter provided with a coating of a hydrophilic acrylate or methacrylate polymer. Infection from the catheter is said to be further reduced by absorbing an antibiotic such as penicillin, bacitracin, and others, or an antibacterial such as hexachlorophene, or a quaternary ammonium compound, in the coating. See also U.S. Pat. No. 3,566,874, issued Mar. 2, 1971.

U.S. Pat. No. 3,663,965, issued May 23, 1972, to H. L. Lee, et al., describes a bacteria-resistant percutaneous conduit device.

U.S. Pat. No. 3,524,447, issued Aug. 18, 1970 to R. P. Evans, et al., discloses a method of making a rigid tipped polyvinyl catheter.

U.S. Pat. No. 3,598,126, issued Aug. 10, 1971, to J. Hoeltzenbein, describes a vascular cannula for medical applications.

U.S. Pat. No. 3,708,324, issued Jan. 2, 1973, to L. F. Stebleton, discloses a method of growing silicone elastomers useful in the manufacture of catheters.

U.S. Pat. No. 3,926,705, issued Dec. 16, 1975, to D. A. Todd, discloses a "Silicone Catheter and Process for Manufacturing Same." See also U.S. Pat. No. 3,983,879.

U.S. Pat. No. 3,886,947, issued June 3, 1975, to P. N. Sawyer, describes a non-thrombogenic catheter.

Belgian Patent 857,264, issued Jan. 30, 1978, to R. L. Stone, describes intravenous solutions comprising aqueous solutions of $C_4$–$C_9$ n-fatty acid antimicrobials. It is the equivalent of copending U.S. application Ser. No. 816,625, filed July 18, 1977, which is a continuation-in-part of application Ser. No. 709,342, filed July 28, 1976, now abandoned.

Copending application Ser. No. 918,532, R. L. Stone, filed June 23, 1978, also discloses solutions containing $C_4$–$C_9$ fatty acid antimicrobials.

DISCLOSURE OF THE INVENTION

The present invention is based on the discovery that certain carboxylate antimicrobial agents, when in contact with permeable polymers, are able to diffuse through the polymers. Thus, by fashioning the walls of medical devices such as catheters from such polymers and passing a solution comprising the carboxylate antimicrobial agent through the lumen of the device, the antimicrobial diffuses through the walls to the external surface of the device to form an antimicrobial barrier on the surface of the device and a zone of microbial inhibition in the tissue surrounding the device, thereby effectively replacing the body's own natural microbial barriers where they have been compromised.

When properly used, the combination of carboxylic acid-permeable polymer catheters with the preferred monocarboxylate (or, simply, "carboxylate") antimicrobials disclosed herein is so effective that it can maintain sterility even during use situations where sterility is normally sacrificed, with the added advantage that the carboxylate antimicrobial acts as a "fail safe" backup for the heat, gas or radiation sterilization procedures normally used in the manufacture of silicone catheters, drains, and the like.

The present invention provides an article of manufacture especially adapted for use as a catheter, or the like, in the bodies of humans or lower animals, comprising: a tube for transporting liquid materials, at least a part of the portion of said tube which contacts the body comprising a carboxylic acid-permeable polymer; said polymer being in contact with both the environment external to said article and with a liquid reservoir of antimicrobial agent flowing through the lumen of said article; said reservoir of antimicrobial agent comprising an aqueous solution containing at least a minimum lethal concentration of a straight-chain carboxylic acid or carboxylic acid salt having from 4 to 9 carbon atoms.

The present invention also provides a method for catheterization with lowered risk of nosocomial infection by achieving microbial inhibition at and around the placement site of catheters and the like used in the bodies of humans and lower animals, comprising inserting into the body of a human or lower animal in need of such treatment a catheter in combination with said liquid reservoir of carboxylate antimicrobial agent, as described hereinabove, whereupon the carboxylic acid antimicrobial passes through the permeable polymer which comprises the walls of the catheter device and establishes a zone of microbial inhibition at and around said catheter.

By "minimum lethal concentration", a term of art in the field of antimicrobial susceptibility testing, is meant the smallest amount of a given antimicrobial agent which will kill microorganisms under the intended conditions of use. Minimum lethal concentrations (or MLC's) can be determined by techniques described in standard reference texts, such as A. L. Barry, *The Antimicrobic Susceptibility Test: Principles and Practices* (1975), the disclosures of which are fully incorporated herein by reference. Minimum lethal concentrations of the carboxylic acids employed in the present invention are disclosed hereinafter.

By "nosocomial infection" herein is meant an infection, either systemic or localized, acquired as a result of hospitalization or treatment while hospitalized, or acquired incident to medical therapy.

By "microbial inhibition" herein is meant the prevention of growth and/or reproduction of viable microorganisms. By "zone of microbial inhibition" or "zone of inhibition" is meant a region containing a sufficient concentration of antimicrobial agent that growth and reproduction of viable microorganisms within the zone is halted.

By "placement site" of a catheter or the like is meant the anatomic path the catheter follows within the body of the human or animal treated, whether such a path is artifically created, as in the case of an intravenous catheter, or exists normally, as in the case of a urinary catheter.

By the term "comprising" herein is meant that various other, compatible ingredients can be present in the articles of this invention as long as the critical components herein disclosed are present. For example, the carboxylate antimicrobial agents used herein can typically be used in sugar, amino acid, electrolyte, etc., solutions of the type well-known for I.V. administration. In use, the sugar, amino acid, etc., solution passes from its reservoir into the patient's body via the catheter, while the carboxylic antimicrobial diffuses through the permeable polymer in the walls of the catheter to provide a zone of microbial inhibition at the catheter placement site. The term "comprising" thus encompasses and includes the more restrictive terms "consisting of" and "consisting essentially of" used to characterize the essential materials used herein.

The critical carboxylate antimicrobials and carboxylic acid-permeable polymers employed in the present invention are defined and described in great detail hereinafter.

All percentages herein are by weight, unless otherwise specified.

BEST MODE

The present invention involves the use of catheter devices fashioned from carboxylic acid-permeable polymers in immediate contact with reservoirs of carboxylate antimicrobials. Variations on the fundamental principles of this invention may be undertaken without departing from the scope and spirit of the invention, as exemplified in the section on Industrial Applicability. However, this invention is best practiced in the following manner.

EXAMPLE I

Highly preferred polymeric catheter materials for use herein are the commercially-available silicone polymers, especially the polydimethylsiloxanes manufactured under "clean" conditions and marketed for various medical uses. Such materials are safe for prolonged use in contact with human tissues and provide excellent diffusion of the preferred carboxylate antimicrobials. As is well known in the art, these silicone polymers can readily be fashioned into catheters designed for a variety of applications. Typical examples of such silicone materials include Silastic ® 382 and Dow Corning ® MDX ® 4-4210, MDX ® 4-4515, MDX ® 4-4516 and Q ® 7-2213, available from the Dow Corning Corporation.

Any of the foregoing carboxylic acid-permeable polydimethyl siloxane polymers are suitable for catheter use and can be formed by standard manufacturing techniques, e.g., extrusion, into tubing which will pass readily through a 16 gauge intravenous needle (I.D. 0.025", O.D. 0.047", equivalent to I.D. 0.635 mm., O.D. 1.1938 mm.). The tubing is fitted with a standard Luer lock hub, packaged and sterilized. In use, the catheter is removed from the package and inserted into a central or peripheral vein using accepted medical techniques. The catheter is connected to an intravenous infusion system in which the intravenous infusion fluid is compounded as follows:

Lactic acid: 2.4 ml.
Sodium hydroxide: 1.15 g.
Sodium chloride: 6.0 g.
Potassium chloride: 0.4 g.
Calcium chloride: 0.4 g.
HCl: to bring solution to pH 5.2
Sodium octanoate: 2.0 g.
Sterile water for injection: qs 1,000 ml.

The sodium hydroxide is dissolved in 200 ml. of the water for injection, the lactic acid is added and the resulting solution is heated in an autoclave at 115° C. for 1 hour and then cooled. The remaining ingredients other than the HCl are dissolved in 700 ml. of the water for injection. The two solutions are mixed, and sufficient dilute HCl and water for injection are added to produce 1,000 ml. of a solution having a pH of 5.2. At this pH the concentration of octanoic acid in protonated (active) form is approximately 3.9 millimolar. Absent the sodium octanoate, the solution is identical to Lactated Ringer's Solution. When this solution is permitted to flow through the silicone cathether previously described into the patient's bloodstream, the solution provides a reservoir of the octanoic acid antimicrobial agent, which diffuses through the silicone polymer of the catheter to provide an antimicrobial barrier on the external surface of the catheter, effectively preventing the surface of the catheter from serving as a route for systemic infection while the patient is receiving the nutrient/antimicrobial solution. The solution is especially effective as an antimicrobial reservoir for articles of the present type when administered at a flow rate of from about 1 ml./hr. to about 1000 ml./hr.

In the solution of Example I, the sodium octanoate is replaced with 114 g. of sodium butyrate and equivalent results are secured.

The sodium octanoate of Example I is replaced with 3.48 g. of hexanoic acid, and equivalent results are secured.

The catheter of Example I is replaced with a catheter made from Dow Corning ® MDS ® 4-4210 Medical Grade Silicone, having an inner diameter of 0.012" (0.3048 mm.) and an outer diameter of 0.025" (0.635 mm.), so that it readily passes through a 19 gauge needle. Identical antimicrobial results are secured.

The catheter of Example I is replaced with a polydimethylsiloxane catheter having an inner diameter of 0.058" (1.4732 mm.) and an outer diameter of 0.077" (1.9558 mm.), which will readily pass through a 12 gauge thin-wall needle. Identical results are secured.

Preferred for use herein are catheters having wall thicknesses of from about 0.002" (0.05 mm.) to about 0.1" (2.5 mm.), although other thicknesses can be used.

Industrial Applicability

Carboxylate Antimicrobials

As will be clear from the following discussion, the selection of an antimicrobial agent which is useful in the present invention requires more than mere knowledge that a particular compound possesses antimicrobial properties. Of course, the antimicrobial must be able to diffuse through the polymeric walls of the catheter. Moreover, the antimicrobial agent must meet several other criteria which are importantly associated with the goal of the present invention—to allow catheterization without risk of related infection.

It is judged extremely important that the antimicrobial agent kill microorganisms quickly, thereby assuring that sterility is promptly and automatically reestablished even in situations where an indwelling catheter is exposed to microorganisms on a continuing basis, e.g., a severely burned patient.

It is also judged that, to be successful, any antimicrobial agent must provide a broad spectrum of kill, due to the variety of microorganisms which have been implicated as causative agents in hospital sepsis.

Therefore, antimicrobial testing was carried out by exposing test microorganisms to various concentrations of antimicrobial agents for short periods of time followed by plating on appropriate media. Screening criteria for selecting suitable antimicrobial agents were as follows:

1. Cell dose
   One log below visual turbidity: ($10^4$ to $10^5$ organisms per ml);
2. Time of exposure to the test antimicrobial agent: Thirty seconds to 5 minutes;
3. Concentration of the test antimicrobial agent: Use of the lowest concentration which satisfies the above two criteria;
4. Test solution: Use of a solution which will support or sustain the metabolism and/or growth of microorganisms;
5. Use of metabolically compatible antimicrobial agents at a physiologically-acceptable pH; and
6. Use of antimicrobial agents which are compatible with the other ingredients of the solutions.

Surprisingly, many compounds reported in the literature as having significant antimicrobial or "preservative" activity did not perform particularly well when tested in aqueous compositions using the foregoing criteria. Included among these compounds were: acetic acid, propionic acid, decanoic acid, undecanoic acid, dodecanoic acid, pivalic acid, iso-hexanoic acid, crotonic acid, 6-aminohexanoic acid, suberic acid, adipic acid, sorbic acid, undecylenic acid, methyl gallic acid, propyl gallic acid, and the methyl, ethyl, propyl and butyl paraben compounds known in the art as preservatives.

Many other known antimicrobials were rejected as clearly being toxicologically unsafe for administration on a continuing bases as required in intravenous therapy or other treatments such as urinary irrigation. These included hexachlorophene, povidone-iodine, phenol, hypochlorite, chlorhexidine, and others.

The antimicrobial agents used herein ("carboxylate antimicrobials") are selected from the non-aromatic water-soluble $C_4$–$C_9$ n-alkyl monocarboxylate acids, or mixtures thereof, or any of their water-soluble, pharmaceutically-acceptable salts. Such salts include, for example, the common water-soluble sodium, potassium, ammonium, etc., salts. The sodium and potassium salts are preferred.

While various carboxylate compounds exhibit different degrees of antimicrobial activity (per mole) in the practice of this invention, the water-soluble n-alkyl $C_4$, $C_5$, $C_6$, $C_7$, $C_8$ and $C_9$ monocarboxylates exhibit excellent antimicrobial activity. The n-hexanoic and n-octanoic acids and pharmaceutically-acceptable, water-soluble salts thereof are much preferred for use herein, due to their ease of use and their broad spectrum antimicrobial activity and speed of kill in solution. The hexanoate and octanoate antimicrobials are highly preferred, with n-octanoate being most highly preferred, inasmuch as these materials in their free acid form rapidly kill essentially all important gram positive and gram negative pathogens and Candida at low solution concentrations in the acid pH range disclosed herein.

The microbiocidal activity of the $C_4$–$C_9$ carboxylate antimicrobials used herein is directly related to the presence of their respective free acids in solution. The concentration of free carboxylic acid in solution, as opposed to carboxylate salt (anionic) form, is a function of the pH of the solution. The carboxylic acid salts can be used herein, but only as long as the pH of the solution is in the acid range so that the minimum lethal concentration (MLC) of free acid is present. Accordingly, the amount of acid or acid salt used will vary somewhat with the use pH. The amount of a given acid or acid salt which will provide the MLC at a given pH will depend on the pKa of the acid. Of course, knowing the pKa, the MLC of the particular acid and the solution pH, the amount of any $C_4$–$C_9$ acid or acid salt to be used is easily calculated from the formula $$pKa = pH + \log \frac{[HC_x]}{[C_x-]},$$

where $[HC_x]$ is the concentration of free acid of chain length x and $[C_x-]$ is the concentration of its anion in solution. For example, with the sodium octanoate antimicrobial the relationship between pH, concentration of sodium salt and percentage of free acid in solution is as shown in Table 1.

TABLE 1

| pH | % Sodium Octanoate | Concentration of Free Acid |
| --- | --- | --- |
| 5.4 | 0.251 | 3.5 millimolar (mM) |
| 4.8 | 0.107 | 3.5 mM |
| 4.4 | 0.078 | 3.5 mM |
| 4.0 | 0.066 | 3.5 mM |
| 3.6 | 0.061 | 3.5 mM |

Microbial testing with n-octanoic acid using the screening criteria disclosed hereinafter has shown that a concentration of about 3 millimolar is the MLC for this acid. The above table specifies the amount of sodium octanoate needed to achieve the MLC of octanoic acid in solution over a range of pH's. In general, the useful concentrations of antimicrobial will fall within the range of from about 100 mM to about 1 M. Of course, concentrations of free acid higher than the MLC can be used.

In like manner, using the MLC's of n-butyric, n-pentanoic, n-hexanoic, n-heptanoic and n-nonanoic acids, together with their pKa's, the amounts of their respective salts required to provide an MLC for each antimicrobial, at any desired solution pH, can be mathematically determined. The MLC values (based on the criteria disclosed herein) for these acids are as follows: $C_4$ 0.4 molar; $C_5$ 0.11 M; $C_6$ 30 mM; $C_7$ 9 mM; $C_9$ 1 mM.

As can be seen from the MLC values, the amounts of the $C_4$ and $C_5$ acids needed to provide a minimum lethal concentration in solution are substantially higher than for the more preferred $C_6$–$C_9$ carboxylic acids. Likewise, at any pH, the concentration of the salts of the $C_4$ and $C_5$ acids needed to reach the free acid MLC will be correspondingly higher than with the $C_6$–$C_9$ acid salts. Since the compositions herein are often used with critically ill patients, it may be important not to overburden the body with excessive amounts of the carboxylates; hence, the $C_4$ and $C_5$ compounds are less preferred than the $C_6$–$C_9$ compounds. Likewise, the $C_7$ and $C_9$ compounds, while they are safely and readily metabolized by the body, are metabolized by secondary pathways due to their having an odd number of carbon atoms and are thus less preferred than the even chain $C_6$ and $C_8$ compounds. As between the $C_8$ and $C_6$ compounds, n-octanoate is preferred over n-hexanoate simply because $C_8$ is more effective (MLC 3 mM vs. MLC 30 mM) on a per-gram basis.

Carboxylates above $C_9$, e.g., decanoates, undecanoates, etc., are not useful herein inasmuch as these compounds are not soluble in water at or above their MLC.

In contrast with the surprising inactivity of many supposedly efficacious antimicrobials under the stringent criteria necessary for parenteral infusions, sodium n-octanoate (pH 5.3) gave the results appearing in Table 2 over an extremely wide spectrum of microorganisms when tested using the criteria discussed above. As can be seen, even without careful control of the test pH, the n-octanoate killed all test organisms within 1.5 minutes; substantially all organisms within 1 minute; and greater than 90% of all organisms within 0.5 minutes of contact.

TABLE 2

Percent of Inoculum Viable After Mixing With 0.2% Sodium Octanoate

| Organism Tested ($10^4$ to $10^5$ per ml) | Time of Exposure (min.) | | | | |
| --- | --- | --- | --- | --- | --- |
| | 0.5 | 1.0 | 1.5 | 2.0 | 2.5 |
| Candida albicans | 0.0 | 0.0 | 0.0 | 0.0 | 0.0 |
| Staphylococcus aureus | 6.1 | 0.005 | 0.0 | 0.0 | 0.0 |
| Streptococcus faecalis | 0.4 | 0.009 | 0.0 | 0.0 | 0.0 |
| Klebsiella pneumoniae | 2.5 | 0.005 | 0.0 | 0.0 | 0.0 |
| Serritia marcescens | 0.002 | 0.0 | 0.0 | 0.0 | 0.0 |
| Escherichia coli | 2.0 | 0.03 | 0.0 | 0.0 | 0.0 |
| Salmonella enteritidis | 2.0 | 0.06 | 0.0 | 0.0 | 0.0 |
| Pseudomonas fluorescens | 0.002 | 0.0 | 0.0 | 0.0 | 0.0 |
| Pseudomonas aeruginosa | 0.02 | 0.0 | 0.0 | 0.0 | 0.0 |

Since patients receiving I.V. therapy often receive considerable volumes of infusion fluid, it is considered essential that the antimicrobial agent present a minimal toxicological load to the already debilitated patient. Ideally, the antimicrobial should be metabolized by primary metabolic pathways of the body to harmless end-products. In this regard, the $C_4$–$C_9$ n-carboxylic acids are virtually unique among the vast array of antimicrobials: they are metabolized, as an energy source, to $CO_2$ and water.

Moreover, an important feature of the $C_4$–$C_9$ n-carboxylic acids is that the pH dependence of their antimicrobial activity means that the acids are immediately converted to the inactive anionic form upon exposure to the pH of the bloodstream. They also bind rapidly to serum proteins, such as albumin, which further renders them inactive once they have served their intended purpose.

Antimicrobial Solutions

The antimicrobial solutions of this invention containing the $C_4$–$C_9$ carboxylic acids can be manufactured under conditions, and using manufacturing procedures, well known in the pharmaceutical field. The base solutions used in the practice of this invention are well known in the industry, and include electrolyte solutions, dextrose solutions, amino acid nutrient solutions, and the like. The solutions herein can be conveniently prepared by simply dissolving sufficient carboxylate salt in the solution to provide at least an MLC of the free acid which corresponds to the salt. As required, the pH of the solution can be adjusted to the range disclosed herein. Standard acetate buffers or other pharmacologically-acceptable buffers can be used for this purpose. The solutions are then packaged and sterilized in standard fashion.

Solutions employed in this invention can be prepared on site by simply dissolving an effective amount of the antifungal/antibacterial carboxylate in a pre-formed solution of the nutritive substance or electrolyte in pyrogen-free water, buffered as needed to provide an appropriate pH for delivery of an MLC of the antimicrobial carboxylate chosen. In general, solutions intended for intravenous infusion should have a pH in the range of from about 3.5 to about 6. This range encompasses the vast majority of commercially available solutions for parenteral injection. Conveniently, many amino acid and/or protein hydrolysate solutions are self-buffering at the pH range 4.9 to 5.2 associated with optimal antimicrobial activity of the $C_4$–$C_9$ carboxylates. In the alternative, the compositions are manufactured and maintained in a closed, sterile container until time of use. Additional sterilization of nutrient solutions comprising carboxylate antimicrobials and sugar can be carried out using heat or filtration techniques well known in the art. Solutions comprising the carboxylate antimicrobials and an amino acid source can likewise be further sterilized by heat or filtration. However, when mixtures of sugars and amino acid sources comprise the nutritive substance, it is preferable to avoid heat sterilization, inasmuch as chemical reactions between sugars and amino acids can occur; accordingly, it is preferable to use filtration techniques to sterilize such solutions. Under these latter circumstances, the added protection afforded by the addition of the carboxylate antimicrobial agents herein is substantial and contributes importantly to the safety of such products.

Nutritive solutions containing albumin-type proteins as a nutritive substance can be stabilized in the manner of the present invention. However, it has been discovered that the albumin proteins can interact with the carboxylic acid antimicrobial agents used in the manner of the present invention and inactivate them. Experiments have shown that one molecule of albumin can interact with, and inactivate, approximately ten molecules of carboxylic acid antimicrobial agent. Accordingly, when stabilizing nutritive compositions containing albumin, it is a simple matter to adjust the usage concentrations of the various carboxylic acid antimicrobials herein to account for the fact that approximately ten moles of the carboxylate will be inactivated by each mole of albumin present in the nutritive composition. The following illustrates this technique.

A sterile, aqueous solution comprising 0.001 moles of bovine serum albumin in 1,000 ml. of water is prepared. The solution is buffered with a sodium acetate/acetic acid buffer and is made 0.010 molar in n-octanoic acid.

A solution of albumin and octanoic acid prepared in the foregoing manner does not exhibit good antimicrobial activity using the test criteria disclosed herein. However, when an additional three millimoles of n-octanoic are added to the solution following addition of the original portion of octanoic acid, excellent antimicrobial activity is secured. It is concluded that the original octanoic acid was bound by the albumin, and once the binding sites on the albumin are filled by the original octanoic acid, the remaining octanoic acid was free to provide the desired antimicrobial activity.

Various commercially-available lipid dispersions approved by the government for intravenous administration are not suitable for use herein, since lipids somehow interefere with the antimicrobial activity of the carboxylates.

Polymeric Catheter Materials

Catheters used in the practice of the present invention can be partly made of any stable material such as glass, plastic, metal, etc., which is not permeable, even to the carboxylate antimicrobial agents. Of course, the catheters should be made from a material which is chemically inert to the solutions being used, as well as to tissues, but selection of inert catheter materials is not a problem. However, it is critical that at least some portion of the wall of the catheters used in the present invention which passes into the body of the patient comprises a polymer which allows permeation of the antimicrobial carboxylic acids therethrough and into the surrounding tissues.

Preferred catheters are those comprising a tube fashioned substantially completely from the carboxylic acid-permeable polymer.

The polymers used in the catheters are characterized by parameters which reflect their strength, integrity and ability to act as a diffusion means through which the $C_4$–$C_9$ n-carboxylate antimicrobial agents can pass (in their acid form).

The catheter materials should be substantially water-insoluble so that they maintain their strength and integrity when in contact with body fluids and the solutions used herein.

Since the catheters are to be used in contact with body fluids and tissues, the carboxylic acid-permeable polymer portion of the catheter (and the total catheter device) should be toxicologically acceptable. Moreover, the overall device, including the carboxylic acid-permeable polymer, will most preferably be immunologically acceptable and will not be rejected by the body's natural defense mechanisms nor have any untoward effect on the rate of antibody formation, and the like.

The catheter must be sufficiently strong, yet flexible, so that it can be guided easily along anatomic passages, where desired.

The catheters employed herein preferably comprise silicone polymers as the carboxylic acid-permeable polymer. Since silicone polymers meet all the above criteria for catheters, it is convenient and preferred that the whole of the catheter device comprise a silicone polymer. The silicone polymers used in preparing the preferred catheters are preferably polydimethysiloxanes, i.e., silicone polymers which contain the repeating unit

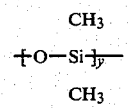

wherein y is an integer in the range of about 100–100,000.

Repeating units of the silicone polymer can contain side-chain branching and cross-linking, e.g.,

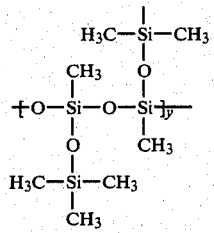

Various functional groups may be present in the basic silicone polymer structure to facilitate cross-linking/curing.

Silicone polymers suitable for use herein can be prepared, for example, by hydrolyzing dimethyldichlorosilane or mixtures of dimethyldichlorosilane, trichloromethylsilane and chlorotrimethylsilane with water, in well-known fashion. Alternatively, siloxane "oligomers" can be polymerized and "cured" in various ways well known in the art. Silicone polymers suitable for preparing the catheters in the present invention are also available commercially, from suppliers such as the Dow Corning Corporation and the General Electric Corporation.

Latex rubbers can also be used as the carboxylic acid-permeable polymer in the present invention. Either the natural or synthetic latex rubber polymers which are commercially available can be used. Such materials include, for example, the isoprene-type rubbers, and the like. Natural or synthetic rubber which is calendered or molded can also be used.

Other types of polymers which can be used as the carboxylic acid-permeable polymer for use in the present invention comprise, for example, polyurethanes; copolymers of silicone polymers and various other polymeric materials such as urethanes, and the like; certain styrene/butadiene copolymers; etc.

However, not all polymer materials are acceptable for use as the carboxylic acid-permeable polymer in the present invention, although such non-permeable polymers can be used as part of the overall catheter. In order to provide sufficient diffusion of the carboxylate antimicrobial to form the desired antimicrobial barrier external to the device (i.e., in the tissue surrounding the entry site of the catheter), a polymer must have a permeability coefficient for the carboxylate antimicrobial being used at least equal to that set forth hereinafter. Where used herein, the term "carboxylic acid-permeable polymer" means a polymer which, in combination with a carboxylate antimicrobial disclosed herein, has a permeability coefficient with respect to the antimicrobial agent at least equal to that indicated in Table 3, herein. Note that the range of operative permeability coefficients is related to the antimicrobial efficacy of the carboxylate. That is, for the more effective (on a per-gram basis) antimicrobial carboxylates, less carboxylic acid must pass through the walls of the catheter to achieve the zone of inhibition than with the less effective antimicrobial carboxylates.

TABLE 3

| Antimicrobial | Permeability Coefficient (acid) |
|---|---|
| n-butyric acid/salt | 3000 nanograms $cm^{-1} hr^{-1}$ |
| n-pentanoic acid/salt | 1200 nanograms $cm^{-1} hr^{-1}$ |
| n-hexanoic acid/salt | 400 nanograms $cm^{-1} hr^{-1}$ |
| n-heptanoic acid/salt | 150 nanograms $cm^{-1} hr^{-1}$ |
| n-octanoic acid/salt | 50 nanograms $cm^{-1} hr^{-1}$ |
| n-nonanoic acid/salt | 15 nanograms $cm^{-1} hr^{-1}$ |

Although either the acid or a pharmaceutically-acceptable salt may be used in solution, it is only the free acid which has antimicrobial activity and which is capable of diffusion through the polymers employed herein.

While not intending to be limited by theory, the permeability of the n-carboxylic acids through some polymers appears to be related in part to the ratio of amorphous phase to crystalline phase within the polymer, the permeability of the n-carboxylic acids involving primarily diffusion through the amorphous phase. Those polymer materials which have sufficiently high amorphous phase:crystalline phase ratios to provide adequate permeability of the n-carboxylate antimicrobials often fall within the broad class known as elastomers. However, knowledge of the precise level of crystallinity in the polymer is not necessary for the selection of carboxylic acid-permeable polymers for use herein, since the permeability coefficient of any polymer can be determined with respect to any of the n-carboxylate antimicrobials used herein by simple, rapid techniques well known to the art, as summarized hereinafter.

The permeability coefficient P' of a polymer sheet in a steady-state system is expressed as $$P' = (Fl/\Delta V),$$

where
F = steady state flux
l = thickness of the polymer sheet
$\Delta V$ = volume fraction difference across the polymer sheet The calculation of the permeability coefficient can be simplified by maintaining the pure antimicrobial on one side of the polymer sheet and distilled water on the other, so that $\Delta V$ is always approximately 1, in which case any technique by which the steady state flux F across a polymer sheet of known thickness l may be measured will allow calculation of the permeability coefficient for any given polymer, as follows.

Polymer Permeability Testing

The permeability of a polydimethyl siloxane polymer to n-octanoic acid is measured in the following manner: Two 40 mm. (dia.)×25 mm. (length) cylinders of stainless steel are machined to provide cavities 16 mm. (dia.)×10 mm. (depth), such that the cavities abut when the two cylinders are clamped together to form a test cell. Each cavity is provided with two inlet holes for filling and sampling.

A 4 cm.×4 cm. sheet of known thickness of the polydimethyl siloxane polymer to be tested is sandwiched between the cylinders, enclosing a 3 mm. glass bead on each side of the sheet to provide stirring. The cell cavities are filled with distilled water and hermetically sealed. After equilibrating overnight at 37° C., the distilled water in one cavity (one half of the cell) is replaced with pure $^{14}$C-n-octanoic acid. The cell is again completely sealed and the cell is maintained at 37° C. in a device which provides 50 rpm axial rotation of the cell. The distilled water in the opposite compartment is periodically removed, sampled, and replaced with fresh distilled water, so that the concentration gradient across the polymer sheet remains approximately 1.

When the solution is removed from the distilled water compartment, a 10 microliter (10 μl) sample is taken by syringe and expressed below the surface of 100 μl of distilled water in a vial for scintillation counting. In the scintillation counting, each sample vial is charged with 10 milliliters (10 ml) of a solution of 0.8% 2-diphenyloxazole and 0.01% of 1,4-bis-[2-(4-methyl-5-phenyloxazolyl)]-benzene in a 1:1 ethanol:toluene mixture. The vials are then placed in the refrigerator compartment of a counting instrument and cooled to 4° C. before being counted for 5 minutes each. The counts per minute are converted to concentrations by applying a factor obtained by counting one or more standard samples. After several samples, the flux of n-octanoic acid across the polymer sheet can be plotted as a function of time and can be seen to become constant as the system reaches a steady-state. The permeability coefficient of the polydimethyl siloxane polymer can then be calculated as described above.

A typical value obtained by this method for the permeability coefficient of polydimethyl siloxane with respect to n-octanoic acid is approximately 750 μg/cm hr, based on a measured steady-state flux of F=13 mg/cm$^2$ hr for a sheet thickness, l, of 0.025" (0.635 mm.). From Table 3 it can be seen that polydimethyl siloxane is therefore an excellent material for use in the present invention, providing a permeability to the antimicrobial agent which is thousands of times greater than the minimum permeability required for use with octanoic acid, and hundreds of times greater than needed for use with butyric acid in the present invention.

It can be seen from the foregoing calculations that thickness of a polymer material of known permeability will determine the flux of antimicrobial across the polymer. Accordingly, the thickness of the catheter wall made from a carboxylic acid-permeable polymer will affect the amount of carboxylate antimicrobial diffusing therethrough. However, diffusion of antimicrobial through the carboxylic acid-permeable polymers of the present invention will be sufficient to establish a zone of microbial inhibition around the catheter, across a wide range of catheter wall thicknesses. In particular, zones of inhibition can readily be established around catheters having wall thicknesses of from about 0.05 mm. to about 2.5 mm., using the materials, methods and flow rates disclosed herein. Below this preferred range, zones of inhibition are easily established, since the flux is large, but mechanical considerations dominate. Above the preferred range, higher flow rates and/or higher concentrations of antimicrobial agent may be necessary to establish a clinically effective zone of inhibition.

However, even with polymer materials having excellent permeability to the n-carboxylate antimicrobials employed herein, establishment of an effective zone of inhibition in the tissues surrounding the catheter requires an adequate rate of delivery of carboxylate antimicrobial to the catheter material for diffusion therethrough. In general, this can easily be accomplished by employing flow rates for the liquid reservoir of antimicrobial agent of from about 1 ml./hr. to about 1,000 ml./hr., although higher flow rates will, of course, also provide an ample liquid reservoir of antimicrobial agent. These flow rates should be achieved as averages when flow of the solution through the catheter is somewhat intermittent. This range of flow rates easily encompasses the infusion rates normally encountered in medical practice. Lower flow rates, which may be encountered in very unusual situations, do not deliver the liquid reservoir of antimicrobial agent to the catheter as rapidly as the antimicrobial agent is depleted from the catheter's exterior surface, and therefore such ultra low flow rates, while providing some measure of antimicrobial protection, are not preferred in the practice of this invention. In unusual situations where low flow rates are used and there is the chance of exhaustion of the carboxylate by diffusion through the catheter into surrounding tissues, the safety of the carboxylates allows higher than normal concentrations to be used in the liquid reservoir, thereby minimizing the chance of reservoir exhaustion.

The following examples illustrate the practice of this invention, but are not intended to be limiting thereof.

EXAMPLE II

A parenteral nutrition solution is prepared according to the following formula:

|  | Grams Per Liter |
|---|---|
| Essential amino acids (crystalline): |  |
| L-lysine | 3.85 |
| L-tryptophan | 0.65 |
| L-phenylalanine | 2.4 |
| Methionine | 2.25 |
| L-leucine | 3.85 |
| L-isoleucine | 2.95 |
| L-valine | 2.8 |
| L-threonine | 1.7 |
| Non-essential amino acids (crystalline): |  |
| Arginine | 1.55 |
| Histidine | 1.2 |
| Glycine | 9.0 |
| Cysteine | 0.1 |
| Proline | 4.75 |
| Alanine | 3.0 |
| Serine | 2.5 |
| Dextrose | 250.0 |
| Sodium hexanoate | 13.0 |
| Potassium (as the phosphate) | 35 mEq. per liter |
| Magnesium (as the sulfate) | 5 mEq. per liter |
| HCl | to bring solution to pH 5.2 |
| Sterile Water for Injection | q.s. |

The solution is administered to a patient in need of hyperalimentation via a silicone catheter inserted in a central vein, as in Example I. The catheter size is selected according to the size of the patient, using the usual medical criteria for catheter selection. The solution is administered at a rate of from 50 to 150 ml./hr. The portion of the sodium hexanoate which has formed free hexanoic acid diffuses through the silicone catheter during the course of administration to form a microbial barrier on the surface of the catheter, and the catheter is thereby prevented from serving as a source of infection. In addition, after the sodium hexanoate and the hexanoic acid produced in solution enter the patient's bloodstream, they are readily metabolized as an additional energy source for the patient.

The sodium hexanoate of the foregoing example is replaced with 175 milligrams of hexanoic acid, and when the sodium content of the solution is adjusted with NaCl, equivalent results are secured.

The sodium hexanoate of Example II is replaced with 0.5 g. of octanoic acid, and equivalent results are secured.

In the foregoing example, the silicone catheter is replaced with a catheter made from one of the following materials: Shell Elexar ® butadiene-styrene copolymer; Steven ® 1880 (MP)CRG polyurethane (ether base); Avcothane ® silicone-urethane copolymer; Dupont Hytrel ® polyester; and Uniroyal ® TPR 1900 ethylene-propylene copolymer. Equivalent results are secured.

EXAMPLE III

Following surgery, a beagle dog is rehydrated with a standard veterinary intravenous solution of 2.5% dextrose and 0.45% NaCl to which has been added 12.8 grams of sodium hexanoate and which has been buffered to pH 5.2. The solution is administered through an intravenous catheter made from USI ® low-density polyethylene. During administration, the hexanoic acid formed in solution (conc. ~ 30 mM) diffuses through the catheter walls to form an external antimicrobial barrier, and I.V.-related infections are thus prevented. The continuous flow of solution provides a reservoir of antimicrobial for the catheter. In addition, the hexanoic acid and salt provide an extra source of energy to the dog when metabolized.

When the catheter of Example III is replaced with carboxylic acid-permeable polypropylene, equivalent results are secured.

EXAMPLE IV

A multiple lumen urinary catheter of silicone rubber is inserted aseptically into the urethra of a human patient in need of catheterization and connected for continuous irrigation with normal saline (0.9 gram % NaCl in Sterile Water for Irrigation). To the normal saline, 0.16 grams per liter of n-nonanoic acid are added and the solution is buffered to pH 5.0 with acetic or citric acid. During continuous irrigation (1 liter/hr.), the saline/nonanoic acid irrigation solution acts as a constant reservoir of antimicrobial.

The n-nonanoic acid diffuses through the silicone rubber of the catheter to establish a zone of microbial inhibition around the catheter and in the urethral mucosa, effectively preventing the occurrence of a catheter-related urinary tract infection in the treated patient. In addition, the antimicrobial solution irrigates the bladder to provide a sterile antimicrobial barrier against retrograde infection of the upper urinary tract.

When the nonanoic acid of the foregoing example is replaced with 5 grams per liter of potassium n-heptanoate, or 11 grams per liter of valeric (n-pentanoic) acid, equivalent results are secured.

EXAMPLE V

An intravenous catheter is manufactured in the following manner: The distal half (the end which connects to the administration set to and at the point of entry into the patient's body) is made from a carboxylate-permeable polymer, such as polydimethylsiloxane. The proximal half (the end inside the patient's body) is made from a non-permeable polytetrafluoroethylene polymer. The two sections are joined with medical-grade adhesive, with their respective lumens end-to-end in axial alignment to provide a single catheter with a continuous lumen.

In use, when an aqueous solution containing an n-alkyl $C_4$-$C_9$ carboxylate antimicrobial agent is flowed through the catheter at a rate of $>1$ ml./hr. to provide a reservoir of antimicrobial for the device, the carboxylate antimicrobial diffuses through the catheter section made from polydimethylsiloxane, establishing a zone of microbial inhibition at the point of entry through the skin. Bacteria are thereby prevented from migrating beyond this point and into the patient's bloodstream.

It can be seen from the foregoing example that the entirety of the catheters employed in the present invention need not be made from a carboxylate-permeable polymer, so long as a portion of the catheter which is in contact with the tissues of the treated human or animal comprises the carboxylate-permeable polymer. Of course, since the point of highest risk of infection is at the site of entry, it is preferred that the carboxylate-permeable polymer be at that site.

What is claimed is:

1. A method for catheterization with lowered risk of nosocomial infection by achieving microbial inhibition at and around the placement site of catheters and the like used in the bodies of humans and lower animals, comprising: inserting into the body of a human or lower animal in need of such treatment a catheter, or the like, said catheter comprising: a liquid reservoir of antimicrobial agent; a delivery means for transporting liquid materials, said delivery means being in the form of a tube; at least part of the portion of said tube which contacts the body comprising a carboxylic acid-permeable polymer, said polymer being in contact with both the environment external to said catheter and with said reservoir of antimicrobial agent flowing within the lumen of said catheter; said reservoir of antimicrobial agent comprising an aqueous solution containing at least a minimum lethal concentration of a straight chain carboxylic acid or carboxylic acid salt having from 4 to 9 carbon atoms.

2. A method according to claim 1 wherein the solution passing through the catheter has a flow rate of from about 1 ml/hr to about 1000 ml/hr.

3. A method according to claim 1 wherein said polymer portion of said catheter has a thickness of from about 0.05 mm. to about 2.5 mm.

4. An article according to claim 1 wherein the carboxylic acid or carboxylic acid salt is present in solution in a concentration of from about 100 $\mu$M to about 1 M.

5. A method according to claim 4 wherein the carboxylic acid or carboxylic acid salt is selected from the group consisting of n-octanoic acid, n-hexanoic acid and their pharmaceutically-acceptable salts, and mixtures thereof.

6. A method according to claim 5 wherein the free hexanoic acid is present in solution in a concentration of at least 30 mM, or the free octanoic acid is present in solution in a concentration of at least 3.5 mM.

7. A method according to claim 4 wherein the solution has a pH of from about 3.5 to about 6.0.

8. An article of manufacture especially adapted for use as a catheter or the like, in the bodies of humans or lower animals, comprising: an aqueous liquid reservoir of antimicrobial agent; a tube for transporting liquid materials, at least a part of the portion of said tube which contacts the body comprising carboxylic acid-permeable polymer, said polymer being in contact with both the environment external to said catheter and with said aqueous liquid reservoir of antimicrobial agent flowing within the lumen of said catheter; said reservoir of antimicrobial agent comprising an aqueous solution containing at least a minimum lethal concentration of a straight chain carboxylic acid or carboxylic acid salt having from 4 to 9 carbon atoms.

9. An article according to claim 8 wherein the carboxylic acid or carboxylic acid salt is present in solution in a concentration of from about 100 µM to about 1 M.

10. An article according to claim 9 wherein the solution of antimicrobial has a pH of from about 3.5 to about 6.0.

11. An article according to claim 9 wherein the carboxylic acid or carboxylic acid salt is selected from the group consisting of octanoic acid, hexanoic acid, and their pharmaceutically-acceptable salts, and mixtures thereof.

12. An article according to claim 10 wherein the free hexanoic acid is present in solution in a concentration of at least 30 mM, or the free octanoic acid is present in solution in a concentration of at least 3.5 mM.

13. An article according to claim 8 wherein the carboxylic acid-permeable polymer portion of the wall of the tube has a thickness of from about 0.05 mm. to about 2.5 mm.

14. An article according to claim 8 wherein the carboxylic acid-permeable polymer is a silicone elastomer.

15. An article according to claim 14 wherein the silicone elastomer is polydimethylsiloxane.

16. An article according to claim 8 wherein the carboxylic acid-permeable polymer is polyethylene.

17. An article according to claim 8 wherein the carboxylic acid-permeable polymer is silicone-urethane copolymer.

18. An article according to claim 8 wherein the carboxylic acid-permeable polymer is ethylene-propylene copolymer.

19. An article according to claim 8 wherein the carboxylic acid-permeable polymer is polyurethane.

20. An article according to claim 8 wherein the carboxylic acid-permeable polymer is polypropylene.

* * * * *